United States Patent
Sorkine et al.

(10) Patent No.: US 7,985,428 B2
(45) Date of Patent: Jul. 26, 2011

(54) METHOD AND COMPOSITION FOR MODULATION OF SYSTEMIC INFLAMMATORY RESPONSES SYNDROME (SIRS)

(75) Inventors: Patrick Sorkine, Ra'anana (IL); Inna Froklis, Kefar Saba (IL); Chaim Locker, Givataim (IL)

(73) Assignee: The Medical Research, Infrastructure, And Health Services Fund Of The Tel Aviv Medical Center, Tel Aviv (IL)

( * ) Notice: Subject to any disclaimer, the term of this patent is extended or adjusted under 35 U.S.C. 154(b) by 1110 days.

(21) Appl. No.: 11/660,089

(22) PCT Filed: Aug. 16, 2005

(86) PCT No.: PCT/IL2005/000890
§ 371 (c)(1),
(2), (4) Date: May 11, 2007

(87) PCT Pub. No.: WO2006/018844
PCT Pub. Date: Feb. 23, 2006

(65) Prior Publication Data
US 2007/0248687 A1    Oct. 25, 2007

Related U.S. Application Data

(60) Provisional application No. 60/601,648, filed on Aug. 16, 2004.

(51) Int. Cl.
*A61K 35/58* (2006.01)
(52) U.S. Cl. .................................................. 424/542

(58) Field of Classification Search ................... 424/542
See application file for complete search history.

(56) References Cited

U.S. PATENT DOCUMENTS

| | | | |
|---|---|---|---|
| 4,341,762 A | 7/1982 | Haast | |
| 6,555,109 B1 | 4/2003 | Shulov et al. | |
| 2002/0031509 A1* | 3/2002 | Ortenheim et al. | 424/94.67 |
| 2003/0175261 A1 | 9/2003 | Weickmann | |

FOREIGN PATENT DOCUMENTS

WO    01/47535    7/2001

OTHER PUBLICATIONS

Cid et al., "Tissue Production of IL-1beta, TNFalfa and IL-6 correlates with the intensity of the systemic inflammatory response (SIR) and with corticosteroid requirements in giant-cell arthritis (GCA)." *FASEB Journal*, v. 18:4-5, Abst. 771.3 (2004).
K. Stocker, "Use of Snake Venom Proteins in Medicine." *Swiss Medical Weekly Review*, v. 129, pp. 205-216 (1999).
Rajendra et al., "Toxins in anti-nociception and anti-inflammation." *Toxicon*, v. 44, pp. 1-17 (2004).
Clissa et al., "The effect of jararhagin, a metalloproteinase from *Bothrops jararaca* venom, on pro-inflammatory cytokines released by murine peritoneal adherent cells." *Toxicon*, v. 39, pp. 1567-1573 (2001).

* cited by examiner

*Primary Examiner* — Ruth Davis
(74) *Attorney, Agent, or Firm* — The Nath Law Group; Susanne M. Hopkins; Ari G. Zytcer

(57) ABSTRACT

The present invention relates to pharmaceutical composition comprising animal venom and using same in a method for the treatment of Systemic Inflammatory Response Syndrome (SIRS) and related pathologies.

6 Claims, 4 Drawing Sheets

METHOD AND COMPOSITION FOR MODULATION OF SYSTEMIC INFLAMMATORY RESPONSES SYNDROME (SIRS)

CROSS-REFERENCE

This is a National Phase Application filed under 35 U.S.C. 371 of International Application No. PCT/IL2005/000890, filed Aug. 16, 2005, claiming the benefit under 35 USC 119(e) of U.S. Provisional Application No. 60/601,648, filed Aug. 16, 2004, the entire contents of each of which is hereby incorporated herein by reference in its entirety.

FIELD OF THE INVENTION

This invention relates to the use of snake venom for modulation of Systemic Inflammatory Response Syndrome. The invention also relates to the prevention of septic shock.

BACKGROUND OF THE INVENTION

Among the most common causes of death in the United States, septic shock (SS) is reported to be the first in non-coronary intensive care units. Physicians have noted that physiologic alternations and organ dysfunction which are commonly seen with bacterial infections, and which may result in SS, could also result from a wide variety of clinical insults which do not originate from any one specific bacterial infection. This clinical state, termed the Systemic Inflammatory Response Syndrome (SIRS) was generally defined by two or more changes in the following four-factors: body temperature, heart rate, respiratory function and peripheral leukocyte count.

SIRS may affect all organ systems and may lead to multiple organ dysfunction syndromes. The hallmark of SIRS is the creation of a proinflammatory state that is marked by tachycardia, tachypnea or hyperpnea, hypotension, hypoperfusion, oliguria, leukocytosis or leucopenia, pyrexia or hypothermia and the need for volume infusion. This condition characteristically does not include a documented source of infection. Metabolic acidosis is a frequent accompaniment to SIRS and it is derived principally from lactate.

The trigger of SIRS is unclear. Advanced competing theories such as second-hit hypothesis, intestine as the motor of SIRS, chaos theory and immunologic inflammation have been suggested as possible theories and mechanism involved in explaining the evolution and/or appearance of SIRS. A few important cell-to-cell signaling molecules have been variably implicated in the genesis of the proinflammatory state. These messengers include among others interleukin IL-1, IL-5, IL-6, IL-8, IL-11, IL-15 and multiple colony stimulating factors, as well as the chemokines.

Similar findings have been made for tumor necrosis factor (TNF)-α and other related molecules that arise from infectious agents such as lipopolysaccharide, staphylococcal enterotoxins A-E and toxic shock syndrome toxin.

TNF-α and β have been extensively studied and have exhibited their role in host defenses against infection and other disease states. The biological effects of the TNFs are mediated through the two membrane associated receptors, TNFR1 (p55) and TNFR2 (p75) that are expressed on the target cells. The postulated pathogenic roles for TNF include sepsis and bacterial and viral pathologies, certain cancers, metastasis and chronic autoimmune disorders such as rheumatoid arthritis, multiple sclerosis and Crohn's disease. The levels of TNF-α was increased in patients with chronic heart failure. TNF-α is an important element in ischemic-reperfusion injury after myocardial revascularization.

To date, the two strategies for inhibiting TNF that have been most extensively studied consist of monoclonal anti-TNF antibodies and soluble TNF receptors (sTNF-R). Both constructs theoretically bind to circulating TNF-α, thereby limiting its ability to engage cell membrane-bound TNF receptors and activate inflammatory pathways.

The best studied of the monoclonal anti-TNF antibodies is infliximab (Remicade®), originally referred to as cA2. Infliximab is a chimeric human/mouse monoclonal anti-TNF-α antibody composed of the constant regions of human (Hu) IgG1$_1$, coupled to the Fv region of a high-affinity neutralizing murine anti-HuTNFa antibody. Because of the potential for an immune reaction to the mouse protein components of a chimeric antibody, an alternate strategy has been to develop a fully human anti-TNF monoclonal antibody. One such antibody, known as D2E7, also known as adalumimab, was generated by phage display technology. A high affinity murine anti-TNF monoclonal antibody was used as a template for guided selection, which involves complete replacement of the murine heavy and light chains with human counterparts and subsequent optimization of the antigen-binding affinity.

In the second approach to TNF inhibition, soluble TNF-R have been engineered as fusion proteins in which the extracellular ligand-binding portion of the huTNF-RI or huTNF-RII was coupled to a human immunoglobulin-like molecule. Although TNF-RI is thought to mediate most of the biological effects of TNF in vivo, engineered sTNF-RI and sTNF-RII constructs both appear to be effective in vivo inhibitors of TNF. Etanercept (sTNF-RII:Fc; Enbrel®) is the best studied of the sTNF-R and is approved for the treatment of rheumatoid arthritis in adults and in children. It is a dimeric construct in which two sTNF-RII (p75) are linked to the Fc portion of human IgG1. The dimeric receptor has a significantly higher affinity for TNF-α than the monomeric receptor (50-1000-fold higher), and the linkage to the Fc structure significantly prolongs the half-life of the construct in vivo. Although it also has an unnatural linkage site, anti-etanercept antibodies have been infrequent. Another mechanism for prolonging the half-life of monomeric receptors is via conjugation with polyethylene glycol.

Animal venom is one of the most amazing and unique adaptations of animal evolution. Venom is a complex mixture of enzymes which prime purpose is to paralyse and digest prey. Substances which are neurotoxic, hemotoxic and proteolytic have been isolated from snake venoms and have been shown to have a somewhat surprising applicability to prophylactic medicine. For example, PCT application WO 01/47535 to Ortenheim et al discloses an antimicrobial composition which comprises at least one snake venom for the prevention, management or treatment of bacterial, fungal, protozoan or viral diseases.

Abbreviations

GOT—glutamic-oxaloacetic transaminase; GPT—glutamic-pyruvic transaminase; IL—interleukin; LDH—lactate dehydrogenase; LPS—lipopolysaccharide; SIRS—systemic inflammatory response syndrome; SS—septic shock; TNF-tumor necrosis factor-α; IL-6 and IL-10—interleukins 6 and 10; WBC—white blood cells.

SUMMARY OF THE INVENTION

The present invention generally stems from the finding that venom of *Vipera Aspis* may be used medicinally. Low dosages of the snake venom may be used to alter the manifestations of, for example, Systemic Inflammatory Response Syndrome (SIRS) and also to prevent, manage and treat such related conditions as septic shock and sepsis. The invention further stems from the surprising finding that such animal venom exhibits inhibition of TNF-α synthesis and release.

The present invention thus provides in one of its aspects, a pharmaceutical composition for the modulation, namely, prevention, management or treatment of non-specific Systemic Inflammatory Response Syndrome (SIRS), septic shock, sepsis, and/or symptoms associated therewith, comprising an effective amount of at least one venom obtained from at least one venomous insect, snake, scorpion or spider, or a combination thereof and a pharmaceutically acceptable carrier, excipient or diluent.

In one embodiment, said at least one venom is obtained from a venomous snake; preferably, a snake selected from Viperidae, Elapidae, Crotolidae, Hydrophidae and Atractaspidae; more preferably from Viperidae snakes and most preferably from the snake *Vipera Aspis*.

In another aspect of the present invention, there is provided a pharmaceutical composition for the modulation, namely, prevention, management or treatment of non-specific SIRS or symptoms associated therewith, which comprises an effective amount of at least two venoms, e.g. from two different groups of snakes, wherein the first venom has an effect on the nervous system and the second venom has an effect on the muscular system, and a pharmaceutically acceptable carrier, excipient or diluent.

The compositions of the invention may be used for the modulation of SIRS of either non-infectious or infectious origins.

In another aspect of the invention, there is provided a pharmaceutical composition comprising snake venom or a fraction thereof obtained from a snake of the Viperidae family. In one embodiment, said snake is *Vipera Aspis*. In another embodiment, said composition is suitable for medical use and further comprises pharmaceutically acceptable carrier, diluent or excipient.

In a further aspect of the present invention, there is provided a use of at least one venom obtained from at least one venomous insect, snake, scorpion or spider, or a combination thereof for the preparation of a pharmaceutical composition for modulating non-specific SIRS, septic shock, sepsis, and/or symptoms associated therewith.

In another aspect of the present invention, there is provided a method of immunizing a mammal against SIRS, septic shock, sepsis, said method comprises: administering to said mammal an effective amount of the venom composition of the present invention, at a suitable dosage.

In yet another aspect, the invention provides an anti-TNF-α composition comprising an effective amount of at least one venom obtained from at least one venomous insect, snake, scorpion or spider, or a combination thereof and a pharmaceutically acceptable carrier, excipient or diluent, said composition being capable of inhibiting synthesis and/or release of TNF-α.

The anti TNF-α composition of the invention inhibits synthesis and/or release of TNF-α, thus modulating SIRS or other TNF-α related pathologies.

In still another aspect, the invention provides a composition comprising an effective amount of at least one venom obtained from at least one venomous insect, snake, scorpion or spider, or a combination thereof and a pharmaceutically acceptable carrier, excipient or diluent, said composition being useful in lowering TNF-α serum concentrations or in blocking the activity of TNF-α in a subject suffering from a disease or disorder associated with increased TNF-α concentrations.

Preferably said at least one venom is obtainable from a venomous snake. More preferably, said snake is selected from Viperidae, Elapidae, Crotolidae, Hydrophidae and Atractaspidae and most preferably from Viperidde snakes.

BRIEF DESCRIPTION OF THE INVENTION

In order to understand the invention and to see how it may be carried out in practice, one preferred embodiment will now be described, by way of non-limiting examples only, with reference to the accompanying drawings, in which.

DESCRIPTION OF THE INVENTION

Figure 1:
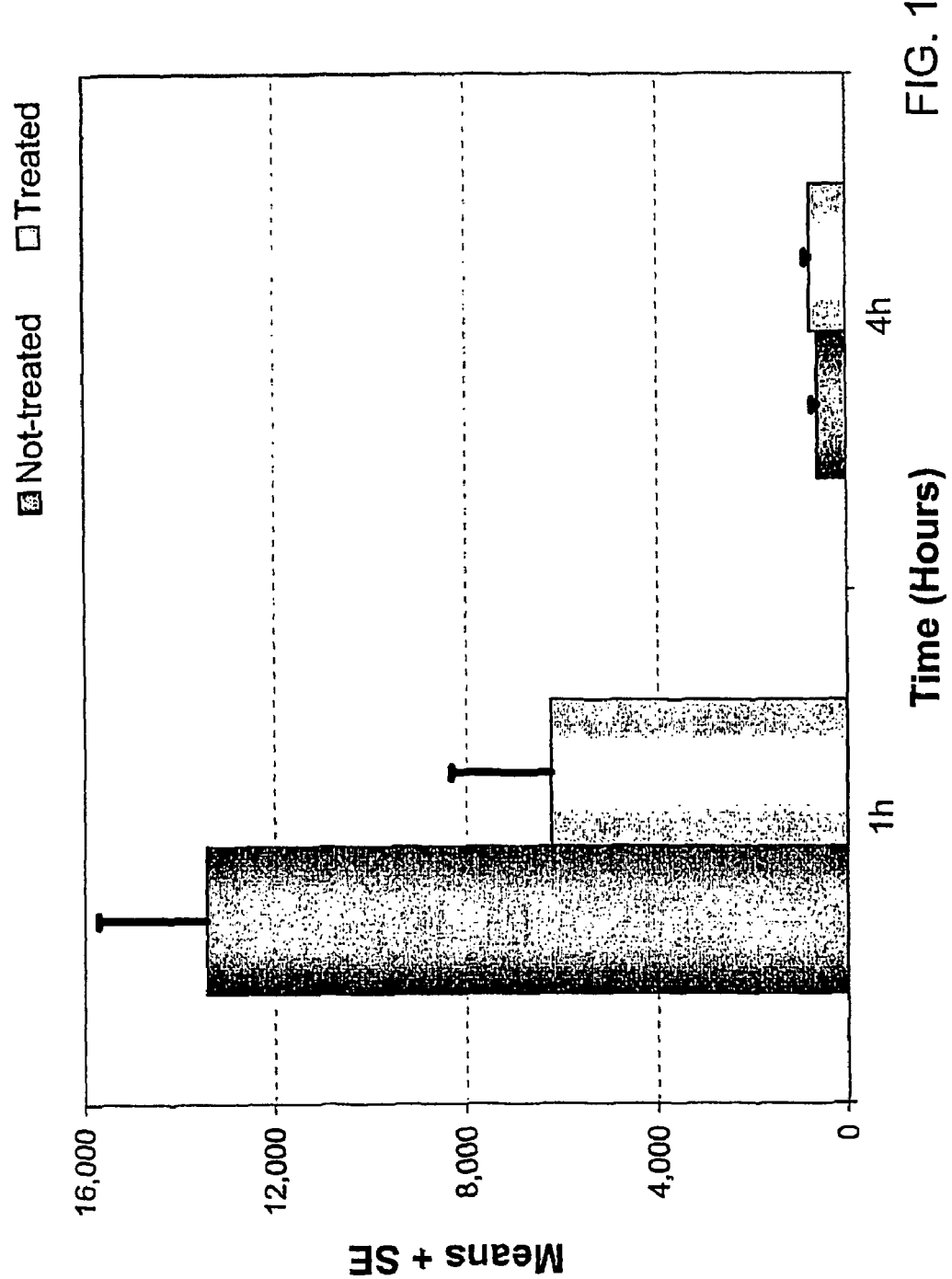
FIG. 1 is a graphic representation of TNF-α serum concentrations at 1 hour and 2 hours post LPS challenge for both the treated group and the control group.

The term "non-specific SIRS" refers to SIRS induced by non-infectious stimuli as well as by infectious stimuli. Non-infectious stimuli may be, for example and without being limited thereto, multiple trauma, severe burns, organ transplantation and pancreatitis and other pathologies known to a person skilled in the art. Infectious stimuli may be Gram-negative or Gram-positive bacteria, fungal, viral and other infections.

Infection with Gram-negative bacteria shows pathological effects which are ascribable to Lipopolysaccharide (LPS), a component of the outer layer of the bacterial membrane capable of causing septic shock by interacting with various components of the host's immune system, particularly macrophages. This immuno-component, releases different endogenous mediators which prove ultimately responsible for the complex pathological picture which ensues.

The fatal outcome of septic shock in humans has recently been linked to the systemic release of substantial amounts of various cytokines, as was described hereinbefore. Tumor Necrosis Factor-α, TNF-O, is the cytokine, which plays a crucial role as mediator in the host's response to LPS. In fact, high levels of TNF-α are found in the serum of animals experimentally intoxicated with LPS, and animals directly inoculated with TNF-α develop a toxic syndrome which is similar to that observed with sepsis.

It has been demonstrated by the inventors of the present invention (Sorkine et al, Intensive Care Med, 2001, 27: 884-888) that treatment of laboratory animals with the venom of *Vipera Aspis* (injected IM), without prior or post challenge with an agent such as LPS, caused a significant increase in serum levels of TNF-α with parallel depressive hemodynamic effects (bradycardia and hypotension). This hemodynamic instability was later shown to stem from TNF-α-mediated cardiac toxicity (Sorkine et al, Crit. Care Med, 2003, 31: 1449-1453).

It has now been shown that when venom such as a snake venom obtained from *Vipera Aspis*, is administered as treatment for septic shock or SIRS associated pathologies, or prior to the development of such conditions, the TNF-α serum concentrations reduce dramatically as compared to non-treated subjects, thus allowing better management of the condition or prevention thereof before clinical symptoms arise.

In a series of studies, the results of which are provided hereinbelow, the mortality and morbidity of laboratory rats pre-treated with snake venom prior to exposure to LPS were compared with the mortality and morbidity of untreated rats. The results showed that there was an apparent significant difference in the mortality rate between the untreated and the treated groups of laboratory rats.

In groups pre-treated by low doses of snake venom prior to LPS exposure, the survival rate was much higher. In the un-treated groups, the survival rate was smaller with all survivors expressing symptoms characteristic of septic shock, namely serious nasal and ocular discharge and "red tears", ruffled fur, anorexia, weight loss, dyspnea, rales and depressed activity.

These results, in combination with results shown hereinfurther, provide a testimony to the ability of the composition of the present invention in modulating, namely, preventing, managing and/or treating conditions such as SIRS. Thus, in one aspect, the present invention provides a pharmaceutical composition for the modulation of non-specific SIRS, i.e. which may be associated with infectious or non-infectious origins, wherein said composition comprises at least one venom obtained from at least one venomous insect, snake, scorpion or spider, or a combination thereof, and a pharmaceutically acceptable carrier, diluent, or excipient. Preferably, the venom is obtained from one or more venomous snake. The venom may be of snakes of the same family or snakes of different families.

The expression "venomous insect, snake, scorpion or spider" refers to any such insect, snake, scorpion or spider which possesses toxic saliva or other fluid which is used as means of protection.

In general, two types of venoms are known: those which include neurotoxins and those which include hemotoxins. Neurotoxin-comprised venoms attack the victim's central nervous system and usually result in heart failure and/or breathing difficulties. Such venom, which contains neurotoxins, may be for example found in cobras, mambas, sea snakes, kraits and coral snakes. Hemotoxic venom attacks the circulatory system and muscle tissue causing excessive scaring, gangrene, and permanent disuse of motor skills and sometimes leads to amputation of the affected area. The Viperidae family such as rattlesnakes, copperheads and cottonmouths are good examples of such snakes.

The venom composition of the present invention may for example include at least one venom of each of the two groups discussed herein, namely, one, which contains neurotoxins and affects the nervous system, and one which contains hemotoxins and affects the muscular system.

Preferably, the venom used in the composition of the present invention is isolated from a variety of venomous snakes from the families Viperidae, Elapidae, Crotolidae, Hydrophidae and Atractaspidae. More preferably it is obtained from the snake family Viperidae and most preferably it is obtained from the species *Vipera Aspis*.

The term "venom" or "venom composition" as used in the context of the present invention relates to whole venom or any part thereof, such as non-specific fraction of the whole venom, a synergistic fraction combination of the whole venom, a combination of one or more agents which are naturally composed in the venom, or a single component thereof which individually or in combination maintain the venom's pharmacological activity as relating to the prevention of non-specific SIRS, septic shock, sepsis. The term also includes any fraction of snake venom, which may be obtained by any fractionation method or synthetic method known to a person skilled in the art. The venom or fractions thereof may be crude, purified or modified.

The term "modulation" or any lingual variation thereof refers to the treatment, management and/or prevention of SIRS or any related condition. The term refers specifically to the avoidance of symptoms before they occur; Such symptoms may be tremor, fever, falling blood pressure, rapid breathing and heart beat, skin lesions, spontaneous clotting in blood vessels, sever hypotension, multiple organ failure and death; to slow down the progression of SIRS, septic shock, sepsis, to ameliorate undesired symptoms associated with the disease or the condition, to slow down the deterioration of symptoms, to enhance the onset of remission period, to slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above.

The composition of the present invention may be administered orally, topically, intraperitoneally, intraarticularly, intracranially, intradermally, intramuscularly, intraocularly, intrathecally, intravenously, or subcutaneously. Other methods known to a person skilled in the art are also applicable. In most cases, the composition may be prepared for parenteral use, for example in a saline solution.

Depending on the formulation used, a suitable pharmaceutically acceptable carrier, excipient or diluent may be used. The pharmaceutically acceptable carriers described herein, for example, vehicles, adjuvants, excipients, or diluents, are well known to those skilled in the art and are readily available to the public. It is preferred that the pharmaceutically acceptable carrier be one which is chemically inert to the active compounds and one which has no detrimental side effects or toxicity under the conditions of use.

The choice of a carrier will be determined in part by the particular constitution of the venom, as well as by the particular method used to administer the composition. Accordingly, there is a wide variety of suitable formulations of the pharmaceutical composition of the present invention.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions.

Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent.

Capsule forms can be of the ordinary hard- or soft-shelled gelatin type containing, for example, surfactants, lubricants, and inert fillers, such as lactose, sucrose, calcium phosphate, and cornstarch.

Tablet forms may include for example one or more of lactose, sucrose, mannitol, corn starch, potato starch, alginic acid, microcrystalline cellulose, acacia, gelatin, guar gum, colloidal silicon dioxide, croscarmellose sodiumk talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers.

Lozenge forms can comprise the venom in a flavor, usually sucrose and acacia or tragacanth, as well as pastilles comprising the venom in an inert base, such as gelatin and glycerin, or sucrose and acacia, emulsions, gels, and the like containing, in addition to the active ingredient, such carriers as are known in the art.

The composition of the present invention may also be made into aerosol formulations to be administered via inhalation. These aerosol formulations may be placed into pressurized acceptable propellants, such as dichlorodifluoromethane, propane, nitrogen, and the like. They may also be formulated as pharmaceuticals for non-pressured preparations, such as in a nebulizer or an atomizer Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. The venom may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly (ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts, and (3) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The venom used in the compositions of the present invention may be made into injectable formulations. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, eds., pages 238-250 (1982), and *ASHP Handbook on Injectable Drugs*, Toissel, 4$^{th}$ ed., pages 622-630 (1986).

Additionally, the compositions of the present invention may be made into suppositories by mixing with a variety of bases, such as emulsifying bases or water-soluble bases.

In yet another embodiment of the present invention, the compositions are also provided with a further component having the capability of stimulating the immune system of the mammal to which the composition is administered. The additional component may be any known immune system stimulator such as immunoglobulins or additional venom, which is known to primarily function by stimulation of the immune mechanism of the body. Such venoms include venoms of the family Viperidae and several genera of the subfamily Crotalinae. One specific example is the venom of *Agkistrodon piscivorus*.

In another aspect of the present invention, there is provided a method for preventing non-specific SIRS, septic shock, sepsis or bactermia in a mammal, said method comprises administering to said mammal an effective amount of a composition comprising at least one venom obtained from venomous snakes, insects, scorpions or spiders.

The present invention further provides a method of treating TNF-α-mediated disease in a mammal comprising administering to said mammal an effective TNF-inhibiting amount of at least one venom as disclosed hereinabove. Such disease may be, without being limited thereto, bacterial, viral or parasitic infections, chronic inflammatory diseases, autoimmune diseases, malignancies, and/or neurodegenerative diseases.

Accordingly, the anti-TNF-α compositions of the present invention have an inhibiting effect against the synthesis TNF-α and may be used in one or more methods for treating and/or diagnosing such pathologies.

TNF-α causes pro-inflammatory actions which result in tissue injury, such as inducing procoagulant activity on vascular endothelial cells, increasing the adherence of neutrophils and lymphocytes, and stimulating the release of platelet activating factor from macrophages, neutrophils and vascular endothelial cells. Recent evidence associates TNF-α with infections, immune disorders, neoplastic pathologies, autoimmune pathologies and graft-versus host pathologies. The association of TNF-α with cancer and infectious pathologies is often related to the host's catabolic state. Cancer patients suffer from weight loss, usually associated with anorexia. The extensive wasting which is associated with cancer, and other diseases, is known as "cachexia" which includes progressive weight loss, anorexia, and persistent erosion of body mass in response to a malignant growth. The fundamental physiological derangement can relate to a decline in food intake relative to energy expenditure. The cachectic state causes most cancer morbidity and mortality. TNF-α can mediate cachexia in cancer, infectious pathology, and other catabolic states.

TNF-α also plays a central role in gram-negative sepsis and endotoxic shock, including fever, malaise, anorexia, and cachexia. Endotoxin strongly activates monocyte/macrophage production and secretion of TNF-α and other cytokines. TNF-α and other monocyte-derived cytokines mediate the metabolic and neurohormonal responses to endotoxin. Endotoxin administration to human volunteers produces acute illness with flu-like symptoms including fever, tachycardia, increased metabolic rate and stress hormone release. Circulating TNF-α increases in patients suffering from Gram-negative sepsis.

Thus, TNF-α related pathologies include, but are not limited to, the following: acute and chronic immune and autoimmune pathologies, such as systemic lupus erythematosus (SLE) rheumatoid arthritis, thyroidosis, graft versus host disease, scleroderma, diabetes mellitus, Graves' disease, Beschet's disease, and the like; infections, including, but not limited to, sepsis syndrome, cachexia, circulatory collapse and shock resulting from acute or chronic bacterial infection, acute and chronic parasitic and/or infectious diseases, bacterial, viral or fungal, such as a HIV, AIDS (including symptoms of cachexia, autoimmune disorders, AIDS dementia complex and infections); inflammatory diseases, such as chronic inflammatory pathologies and vascular inflammatory pathologies, including chronic inflammatory pathologies such as sarcoidosis, chronic inflammatory bowel disease, ulcerative colitis, and Crohn's pathology and vascular inflammatory pathologies, such as, but not limited to, disseminated intravascular coagulation, atherosclerosis, and Kawasaki's pathology; neurodegenerative diseases, including, but are not limited to, demyelinating diseases, such as multiple sclerosis and acute transverse myelitis; extrapyramidal and cerebellar disorders such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo palsy; Cerebellar and Spinocerebellar Disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and Machadojoseph)); and systemic disorders (Refsum's disease, abetalipoprotemia, ataxia, telangiectasia, and mitochondrial multi system disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, or any subset thereof; malignant pathologies involving TNF-secreting tumors or other malignancies involving TNF, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or Mycosis fungoides)); carcinomas (such as colon carcinoma) and metastases thereof; cancer-related angiogenesis; infantile haemangiomas; alcohol-induced hepatitis; and other diseases related to angiogenesis or VEGF/VPF, such as ocular neovascularization, psoriasis, duodenal ulcers, angiogenesis of the female reproductive tract, chronic heart failure, myocardial revascularization, ischemic-reperfusion injury.

The anti-TNF-α compositions may also act to alter or cease TNF-α synthesis or release thereof into the blood stream and thus result in the lowering of serum concentrations as compared to an untreated model.

Without wishing to be bound by theory, lowering of serum concentrations of TNF-α by venom may be achievable by inhibiting TNF-α synthesis, inhibiting TNF-α processing and release, inhibiting effects exerted by TNF-α, or other mechanisms or any combination of two or more mechanisms.

The expression "inhibiting TNF-α synthesis, inhibiting TNF-α processing and release, inhibiting effects exerted by TNF-α" refers to the ability of the venom to block at least one biological activity of TNF-α, such as preventing TNF-α from binding to a TNF-α receptor, blocking production of TNF by intracellular processing, such as transcription, translation or post-translational modification, expression on the cell surface, secretion or assembly of the bioactive trimer of TNF-α. Additionally, venom can act by inducing regulation of metabolic pathways such as those involving the up or down regulation of TNF-α production. Alternatively the venom can modulate cellular sensitivity to TNF-α by decreasing such sensitivity. Such inhibition or neutralization of TNF-α activity may be in vitro, in situ or in vivo.

Screening methods which may be used to determine TNF-α synthesis inhibition or neutralizing thereof caused by the activity of certain venom or a certain effective amount thereof may include in vitro or in vivo assays. Such in vitro assays may include a TNF-α cytotoxicity assay, such as a radioimmuno assay which determines a decrease in cell death by contact with TNF-α, such as human TNF-α in isolated or recombinant form, wherein the concurrent presence of the venom reduces the degree or rate of cell death. Cell death may be determined using $ID_{50}$ values which represent the concentration of the venom which is capable of decreasing the cell death rate by 50%. Another in vitro assay which can be used to determine the inhibitory or neutralizing activity of an effective amount of the venom is an assay which measures the inhibition or neutralization of TNF-α induced procoagulant activity. Other methods may be is determined by routine experimentation based on the knowledge of those skilled in the art.

The compositions of the present invention comprise venom in effective but non-toxic dosages. As a non-limiting example, treatment of TNF-α-related pathologies such as those mentioned hereinbefore, in humans or animals can be provided as a daily dosage of the venom in an amount ranging from 0.1 to 100 mg/kg. Such dosages may be 0.5, 0.9, 1.0, 1.5, 2, 3, 4, 5, 6, 7, 8, 9, 10, 15, 20, 30, 40, 45, 50, 60, 70, 80, 90 or 100 mg/kg, per day, or alternatively, per week, or in any combination using single or divided doses.

Dosage forms (composition) suitable for internal administration generally contain from about 0.1 milligram to about 500 milligrams of the venom per unit. In the pharmaceutical compositions of the present invention, the venom may be present in any effective amount which may affect the required clinical picture.

The term "effective amount" for purposes herein disclosed is determined by such considerations as may be known in the art. The effective amount is typically determined in appropriately designed clinical trials (dose range studies) and the person versed in the art will know how to properly conduct such trials in order to determine the effective amount. As generally known, an effective amount depends on a variety of factors including distribution profile of the venom within the body, a variety of pharmacological parameters such as half life in the body, on undesired side effects, if any, on factors such as age and gender, and the like.

The composition may be administered alone or in combination with other known compositions such as analgesics and antibiotics. The composition may also be administered prior to a surgical procedure such as organ transplantation or other invasive or non-invasive procedures in order to down-regulate or up-regulate mechanisms which may be involved in inducing SIRS.

Materials and Methods

Venoms—

*Vipera Aspis* venom was obtained as a dry powder from Unite des Venins, Institut Pasteur, Paris, France)

Assays—

Wistar rats of similar age and weighting on average 300-350 grams each were randomly divided into five groups.

The first group comprising 70 subjects, hereinafter referred to as the treated group was injected intramuscularly with 100 µg/kg *Vipera Aspis* venom in saline, once daily for a period of 9 days with pause on days 6 and 7.

The second group comprising 70 subjects, referred to herein as the control group was injected with saline only, simultaneously with the treated group.

The test for modulation of SIRS was conducted two weeks thereafter. In a typical test, the rats of both groups were injected once intraperitoneally with 15 mg/kg of lipopolysaccharide (LPS), thereby inducing septic shock. The rats were monitored over a 2-day period (1 h, 6 h, 24 h and 48 h) for LPS induced symptoms such as fever, hypotension, disseminated intravascular coagulation, and multiple organ system failure. As LPS binds to several receptors on leukocytes which results in a cascade of events, increased release of cytokines such as tumor necrosis factor-a (TNF-α), interleukin 6 and 10 (IL-6 and IL-10) was monitored as well.

The third group comprising 20 subjects, referred to herein as the treated control group, was injected intramuscularly with 100 µg/kg *Vipera Aspis* venom in saline, once daily for a period of 9 days with a pause on days 6 and 7 simultaneously with the other groups and was used as a control for delay influence of the venom. This group of 20 subjects received intraperetionally normal saline instead of LPS after two weeks and was studied simultaneously with the treated and control groups in two time points: two weeks and two weeks +48 hours.

The fourth group consisted of 40 subjects, referred herein as the untreated control group, was injected intramuscularly normal saline instead of the venom, once daily, for a period of 9 days and after two weeks received intraperetonially normal saline instead of LPS. This group was studied simultaneously with the other groups.

The fifth group consisted of 30 subjects, referred herein as the venom group, and served as a control for the immediate venom effect. The rats were injected intramuscularly with 100 µg/kg *Vipera Aspis* venom, once daily over a period of 9 days, as with the treated group. The rats were examined an hour after venom injection on days 1, 5 and 9 of the experiment.

Table 1 summarizes the various test groups used.

TABLE 1

Test groups of rats.

| Group # | Group Name | Number of subjects | Experimental agent | Challenge agent |
|---|---|---|---|---|
| 1 | Treated group | 70 | Venom | LPS |
| 2 | Control group | 70 | Saline | LPS |
| 3 | Treated control group | 20 | Venom | Saline |
| 4 | Untreated control group | 40 | Saline | Saline |
| 5 | Venom group | 30 | Venom | — |

Results—

Mortality and Morbidity Tests—

The ability of the venom treatment in down regulating SIRS was evident from the following results:

Control group: n=110; within 6 hours from LPS challenge 10% of the rats in this group died. One day after LPS challenge a total of 41% of the rat population died and within two days from LPS challenge 45.5% of the rats in the control group died with the remaining showing behavior typical of or that may be associated with septic shock. The behavior included: serious nasal and ocular discharge and "red tears", ruffled fur, anorexia, weight loss, dyspnea, rates and depressed activity.

Treated groups: n=85; within 6 hours from LPS challenge only 1.2% of the rat population died. One day after challenge the mortality was 24.6% and remained constant for the remaining experiment. In contrast to the behavior exhibited by the surviving subject of the control group, the surviving subjects of the treated group did not show any symptoms which could have been associated with LPS toxicity.

Blood and Tissue Sampling

The rats were anesthetized by intraperitoneal injection of 60 mg/kg ketamine chloride. Blood samples (6-7 ml) were taken from posterior vena cava after laparotomia and then proportionally divided to determine cytokines and to provide routine chemistry and hematology tests. Simultaneously, the specimens of lung, liver, heart and kidney of the killed animals were rapidly excised and placed in a 10% solution of formaldehyde for standard fixation. Microthin sections were taken and stained with hermatoxylin and eosin for light microscopic analysis. The blood and tissue samples were taken in time periods as stated above.

Blood samples to cytokine determination were immediately centrifuged (15,000 rpm) for 15 minutes at 4° C. and the serum was frozen at −70° C. until analyzed. TNF, IL-6 and IL-10 levels were measured by a commercially available ELISA kits (Quantikine kit for Rat TNF-α Immunoassay, Quantikine kit for Rat IL-6 Immunoassay and Quantikine kit for Rat il-10 Immunoassay, R&D System, Minneapolis, USA)

As Table 2 shows, rats that were challenged with LPS after having received a dosage of the venom secreted smaller amounts of TNF-α as compared to the rats in the control group. A similar conclusion may be drawn from FIG. 1. Additionally, as Table 3 shows, after venom injection and in the absence of LPS challenge, the rats developed tolerance to the venom which was manifested in a decrease in the concentration of TNF-α in the serum even after a continued daily injection of the venom. Simultaneously therewith, the concentrations of IL-6 continued to rise with no exhibited tolerance to the IL-6.

TABLE 2 cytokines serum concentrations (pg/ml) in treated versus untreated rat population.

| | LPS 1 h | LPS 4 h | LPS 24 h | LPS 48 h |
|---|---|---|---|---|
| | IL-10 pg/ml | | | |
| Treated group | 290 ± 34.83 | 1292 ± 571.9 | 129 ± 43.34 | 45 ± 27 |
| Control group | 343 ± 121.6 | 1393 ± 263.9 | 112 ± 23.06 | 28 ± 19.02 |

TABLE 2-continued cytokines serum concentrations (pg/ml) in treated versus untreated rat population.

|  | LPS 1 h | LPS 4 h | LPS 24 h | LPS 48 h |
|---|---|---|---|---|
| | | IL-6 pg/ml | | |
| Treated group | 739 ± 478.8 | 75371 ± 24853 | 404.4 ± 158.2 | 154.8 ± 40.3 |
| Control group | 1557 ± 1397 | 87796 ± 33789 | 507 ± 430 | 297 ± 257 |
| | | TNF-α | | |
| Treated group | 7393 ± 2199 | 607 ± 34.83 | Under detected | Under detected |
| Control group | 12960 ± 738 | 518 ± 85.26 | Under detected | Under detected |

Since circulating concentrations of TNF-α tend to be extremely low, or can only be detectable at sites of TNF-α-mediated pathology in the range of about 10 pg/ml in non-septic individuals, and reaching about 50 pg/ml in septic patients and above 100 pg/ml in the sepsis syndrome, the concentrations observed in for the untreated control attest to the simulated septic state which was brought about by an LPS injection.

The presented results exhibit a state in which administering the venom caused a reduction in pro-inflammatory cytokines such as TNF-α without effecting anti-inflammatory cytokines such as IL-10. This is a unique situation as it is normally expected that increasing amounts of pro-inflammatory cytokines would result in an increase in anti-inflammatory agents. Not only that such an increase was not observed, but also the reduction of TNF-α levels did not reach dangerously low levels with any development of side effects. The irresponsiveness of IL-6 to the treatment and the fact that mortality was low further provided an indication that such venom concentrations used were not toxic to the animals.

TABLE 3 serum concentrations (pg/ml) of cytokines measured one hour after venom injections on days 1, 5 and 9 of the experiment without an LPS challenge.

|  | Day 1 | Day 5 | Day 9 |
|---|---|---|---|
| IL-10 | Under detected | Under detected | Under detected |
| IL-6 | 225 ± 165.9 | 796 ± 70.2 | 893 ± 251 |
| TNF-α | 123 ± 27.27 | 67 ± 38.68 | 25 ± 21.1 |

When the pro-inflammatory TNF-α index was calculated, a similar trend was observed. Table 4 summarizes the averaged index (TNF-α max/IL-10 max) for the treated and control groups. As may be concluded therefrom, upon treating LPS challenged rats with the venom, the concentration of the pro-inflammatory TNF-α reduced with no significant reduction in the concentrations of the anti-inflammatory IL-10.

TABLE 4 pro-inflammatory TNF-α index (TNF-α max/IL-10 max)

| TREATED | | UNTREATED | |
|---|---|---|---|
| TNF-α concentration | IL-10 concentration | TNF-α concentration | IL-10 concentration |
| 24.64 | 16.43 | 37.03 | 16.2 |
| 29.57 | 5.099 | 21.6 | 3.757 |
| 5.099 | 13.44 | 25.92 | 6.322 |
| 5.281 | 6.721 | 7.855 | 1.979 |
| 6.049 | 6.654 | 19.44 | 10.6 |
| 2.42 | 4.293 | 19.44 | 10.6 |

TABLE 4-continued pro-inflammatory TNF-α index (TNF-α max/IL-10 max)

| | TREATED | | UNTREATED | |
|---|---|---|---|---|
| | TNF-α concentration | IL-10 concentration | TNF-α concentration | IL-10 concentration |
| | 9.505 | 5.545 | 14.58 | 25.92 |
| | 4.436 | 2.609 | 21.21 | 33.33 |
| Index | 9.237 | | 17.68 | |
| SD | 5.926 | | 8.327 | |
| P | 0.016 | | | |

Routine hematology tests of the blood samples (leukocytes, red blood cell, platelets, hemoglobin, hematocrit) of the various treated and control groups was evaluated as well. Two weeks after treatment with the venom it had limited effect on the various blood components (results not shown). Nevertheless, LPS challenge significantly affected the leukocyte (WBC) count.

Figure 2:
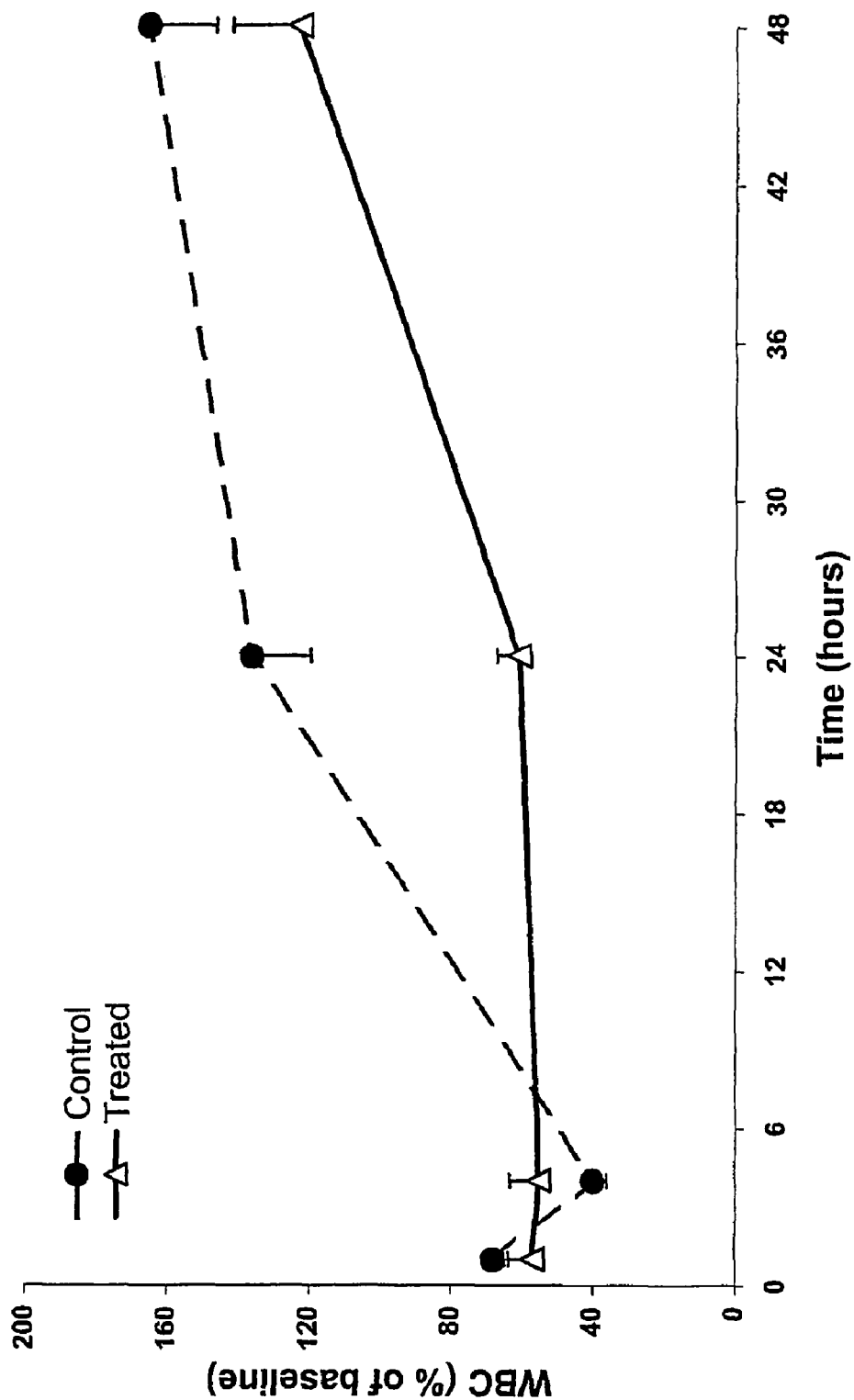
FIG. 2 is a graphic representation of white blood cell count immediately post LPS challenge.

As FIG. 2 shows, 1 hour after LPS challenge the control non-treated group showed a decrease in leukocyte concentration as a result of initial leukocyte infiltration of organ tissues such as the lung, kidney and heart (histological pictures not shown). In the lungs of rats in the control group, for example, the leukocyte concentration was 942% greater (as compared to control) 1 hour post LPS challenge and 3429% greater at the 48-hour mark. In the treated group, the leukocyte concentration 1 hour post LPS challenge was 362% greater and 128% greater at the 48-hour mark. Such a distribution in the treated group was minor.

Four hours post challenge, a dramatic nearly 4-fold increase in the leukocyte concentration was observed in the control group, leading to the death of half of the population within that period. In the treated group, such a drastic increase was not observed.

LPS challenge causes a decrease of platelet count (in ml) both in the control and treated groups from 875400±107040 to 16333±8689 and from 809555±170025 to 15333±1345, respectively, during the 24-hour period. After 48 hours, there was a significant increase of platelet count in treated group in comparison to the 24-hour period (196285±1404, P=0.03), and in comparison to the control group at the same time point (16325±1386).

After venom injection and in the absence of LPS challenge, the rats developed tolerance to the venom which was manifested in return of WBC count to control ranges even after a continued daily injection of the venom.

Blood chemistry of the various treated and control groups was evaluated as well. As Table 5 show, after two weeks of treatment with the venom, it had limited effect on the various blood components LPS challenge caused changes in all blood chemistry parameters (Tables 6-7), but there were no significant differences in most of these parameters between the control and treated groups, with the exclusion of LDH that was significantly higher in the control group (in percents, $P=0.03$, two-way analysis of variance).

Most of the blood chemistry parameters in the control group were significant higher as compared with the untreated control group at the same time point.

Additionally, as Table 7 A and B show, after venom injection and in the absence of LPS challenge, the rats developed tolerance to the venom which showed parameters similar to those of the control even after a continued daily injection of the venom.

TABLE 5

Blood chemistry of untreated versus treated control groups. The numbers in bold are the amount of each component in the blood. The numbers not in bold are the standard deviation values. BUN- urea.

| BUN mg/dl | creatinine mg/dl | sodium mmol/l | chloride mmol/l | calcium mg/dl | LDH U/l | GOT U/l | alk. Phos U/l | GPT U/l |
|---|---|---|---|---|---|---|---|---|
| Untreated Control Group (saline and challenge with saline) | | | | | | | | |
| 16.8 | 0.64 | 151 | 106.6 | 9.7 | 711.6 | 99.52 | 170.7 | 67.65 |
| 2.85 | 0.05 | 11.99 | 7.6 | 0.61 | 304.2 | 22.5 | 31.8 | 14.48 |
| Treated Control Group (venom and challenge with saline) | | | | | | | | |
| 18.6 | 0.6 | 145.05 | 101.63 | 9.73 | 1029.2 | 119.21 | 170.05 | 67.35 |
| 3.31 | 0.04 | 4.64 | 46.64 | 0.51 | 348.21 | 35.07 | 30.87 | 10.21 |

TABLE 6

Blood chemistry of treated with LPS challenge group versus untreated challenges control groups. The numbers in bold are the amount of each component in the blood. The numbers not in bold are the standard deviation values. BUN- urea.

| BUN mg/dl | creatinine mg/dl | sodium mmol/l | chloride mmol/l | calcium mg/dl | LDH U/l | GOT U/l | alk. Phos U/l | GPT U/l |
|---|---|---|---|---|---|---|---|---|
| Control Group (saline and challenge with LPS) | | | | | | | | |
| 1 h | | | | | | | | |
| 18.8 | 0.705 | 100.7 | 100.7 | 9.422 | 381.7 | 89.55 | 202.8 | 58.3 |
| 2.36 | 0.0714 | 1.13 | 2.68 | 0.2 | 103.3 | 24.43 | 67.66 | 9.43 |
| 4 h | | | | | | | | |
| 30.2 | 0.756 | 144.1 | 100.4 | 9.14 | 1094 | 203.7 | 175 | 99.4 |
| 6.42 | 0.12 | 1.55 | 1.89 | 0.32 | 538.1 | 121.4 | 60.75 | 51.4 |
| 24 h | | | | | | | | |
| 64.2 | 0.729 | 144.1 | 105.6 | 9.05 | 965.1 | 462.7 | 383.3 | 311 |
| 45.8 | 0.08 | 2.96 | 4.27 | 0.48 | 322.6 | 462.7 | 156.0 | 44.6 |
| 48 h | | | | | | | | |
| 27.1 | 0.705 | 148.12 | 103.25 | 9.9 | 1382.5 | 180.1 | 181 | 110 |
| 7.39 | 0.08 | 4.12 | 3.88 | 0.34 | 678.1 | 91.55 | 45.82 | 34.9 |
| Treated Group (venom and challenge with LPS) | | | | | | | | |
| 1 h | | | | | | | | |
| 18 | 0.66 | 142.4 | 102.6 | 9.45 | 609.88 | 98.33 | 181.55 | 65.11 |
| 1.73 | 0.06 | 1.5 | 1.5 | 0.20 | 267.21 | 42.98 | 35.14 | 11.78 |
| 4 h | | | | | | | | |
| 29.7 | 0.85 | 143.4 | 102.3 | 9.52 | 1989.5 | 251.3 | 203.3 | 138.9 |
| 3.97 | 0.11 | 1.7 | 2.2 | 0.24 | 250.59 | 44.37 | 39.85 | 10.78 |
| 24 h | | | | | | | | |
| 56.3 | 0.72 | 143.8 | 104.5 | 9.26 | 990 | 849.7 | 359.7 | 717.7 |
| 21.12 | 0.06 | 1.3 | 1.3 | 0.32 | 246.87 | 46.52 | 30.74 | 11.75 |
| 48 h | | | | | | | | |
| 30.14 | 0.71 | 145.5 | 101 | 9.9 | 1239.4 | 125.7 | 157 | 60.57 |
| 12.7 | 0.08 | 2.9 | 2.1 | 0.43 | 216.69 | 40.55 | 30.30 | 12.63 |

TABLE 7A

Blood chemistry of control group treated with saline only. Chemistry was performed on days 1, 5 and 9 of the experiment. The numbers in bold are the amounts of the components in the blood. The numbers not in bold are the standard deviation values. BUN- urea.

| BUN mg/dl | creatinine mg/dl | sodium mmol/l | chloride mmol/l | calcium mg/dl | LDH U/l | GOT U/l | alk. Phos U/l | GPT U/l |
|---|---|---|---|---|---|---|---|---|
| 1 day control (saline only) | | | | | | | | |
| 17 | 0.69 | 169 | 117 | 10.62 | 560 | 99 | 183.8 | 76.6 |
| 1.2 | 0.03 | 6 | 4.8 | 0.42 | 122.8 | 17.2 | 14.96 | 14.32 |
| 5 day control (saline only) | | | | | | | | |
| 15 | 0.634 | 141.2 | 101.8 | 9.36 | 728.6 | 91 | 143 | 59.2 |
| 2.32 | 0.068 | 0.96 | 0.64 | 0.08 | 183.7 | 23.6 | 20.4 | 7.44 |
| 9 day control (saline only) | | | | | | | | |
| 17.3 | 0.618 | 147 | 103.9 | 9.46 | | 104.5 | 178.1 | 67.4 |
| 2.96 | 0.02 | 3.8 | 3.7 | 0.12 | 105 | 14.51 | 24.28 | 8.08 |

TABLE 7B

Blood chemistry of the venom group treated with venom only; no challenge followed. Chemistry was performed on days 1, 5 and 9 of the experiment. The numbers in bold are the amounts of each component in the blood. The numbers not in bold are the standard deviation values. BUN- urea. Venom group (venom with no challenge)

| BUN mg/dl | creatinine mg/dl | sodium mmol/l | chloride mmol/l | calcium mg/dl | LDH U/l | GOT U/l | alk. Phos U/l | GPT U/l |
|---|---|---|---|---|---|---|---|---|
| day 1 | | | | | | | | |
| 27.6 | 1.05 | 198.8 | 140.2 | 12.64 | 1632 | 151 | 207.4 | 78.6 |
| 4.04 | 0.06 | 8.5 | 6.487 | 1.18 | 270 | 23 | 54.26 | 14.81 |
| day 5 | | | | | | | | |
| 17.4 | 0.61 | 141.2 | 362 | 9.76 | 1530 | 117 | 128.6 | 55.6 |
| 3.71 | 0.03 | 2.1 | 180.82 | 0.19 | 786 | 28 | 29.8 | 13.59 |
| day 9 | | | | | | | | |
| 19.6 | 0.68 | 140.4 | 101.4 | 9.56 | 1124 | 96 | 105.4 | 63.2 |
| 2.7 | 0.07 | 1.1 | 0.8 | 0.05 | 357 | 15 | 7.8 | 16.47 |

Pearson correlation between white blood cell (WBC) count and TNF-α concentration showed no significant correlation in the control group, 1 or 4 hours post LPS challenge (Table 8A). A correlation between LDH, GOP, GOT and INF-α was also absent. This means that TNF-α concentration fluctuations were independent of fluctuations in the concentration of either the white blood cell concentration or LDH concentration. There was no observable relationship between a possible decrease in TNF-α concentration and a similar decrease in the LDH, GOP and GOT concentration or WBC count.

TABLE 8A

Pearson correlation for TNF-α of control group.

| | | LDH | GOT | GPT | WBC |
|---|---|---|---|---|---|
| Pearson | 1 hour | −0.399 | 0.121 | 0.011 | 0.290 |
| Correlation r | 4 hours | 0.275 | 0.266 | 0.167 | 0.327 |
| Sig. | 1 hour | 0.434 | 0.796 | 0.981 | 0.485 |
| (2-tailed) | 4 hours | 0.510 | 0.524 | 0.693 | 0.474 |
| Number of | 1 hour | 6 | 7 | 7 | 8 |
| subjects | 4 hours | 8 | 8 | 8 | 7 |

LDH—Lactate dehydrogenase; GOT—Glutamic-oxaloacetic transaminase; GPT—Glutamic-pyruvic transaminase; WBC—white blood cells.

TABLE 8B

Pearson correlation for TNF-α of treated group.

| | | LDH | GOT | GPT | WBC |
|---|---|---|---|---|---|
| Pearson | 1 hour | −0.856 | 0.791 | 0.774 | −0.854 |
| Correlation r | 4 hours | 0.878 | 0.866 | 0.856 | 0.746 |
| Sig. | 1 hour | 0.014 | 0.034 | 0.041 | 0.007 |
| (2-tailed) | 4 hours | 0.004 | 0.005 | 0.007 | 0.034 |
| Number of | 1 hour | 7 | 7 | 7 | 8 |
| subjects | 4 hours | 8 | 8 | 8 | 8 |

Figure 3:
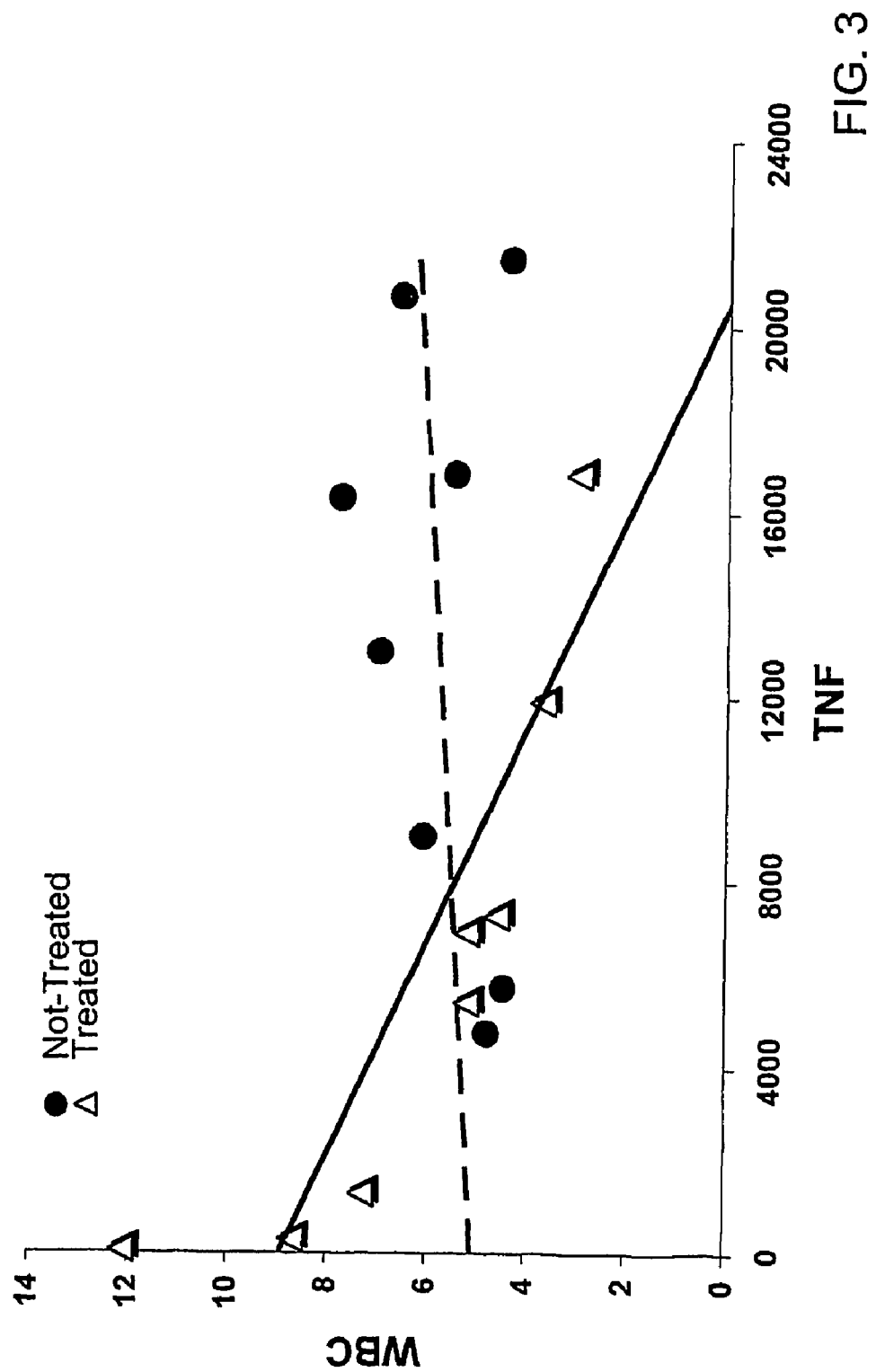
FIG. 3 is a graphic representation of white blood cell count versus TNF-α count for both the treated and control groups, one hour post LPS challenge.
Figure 4:
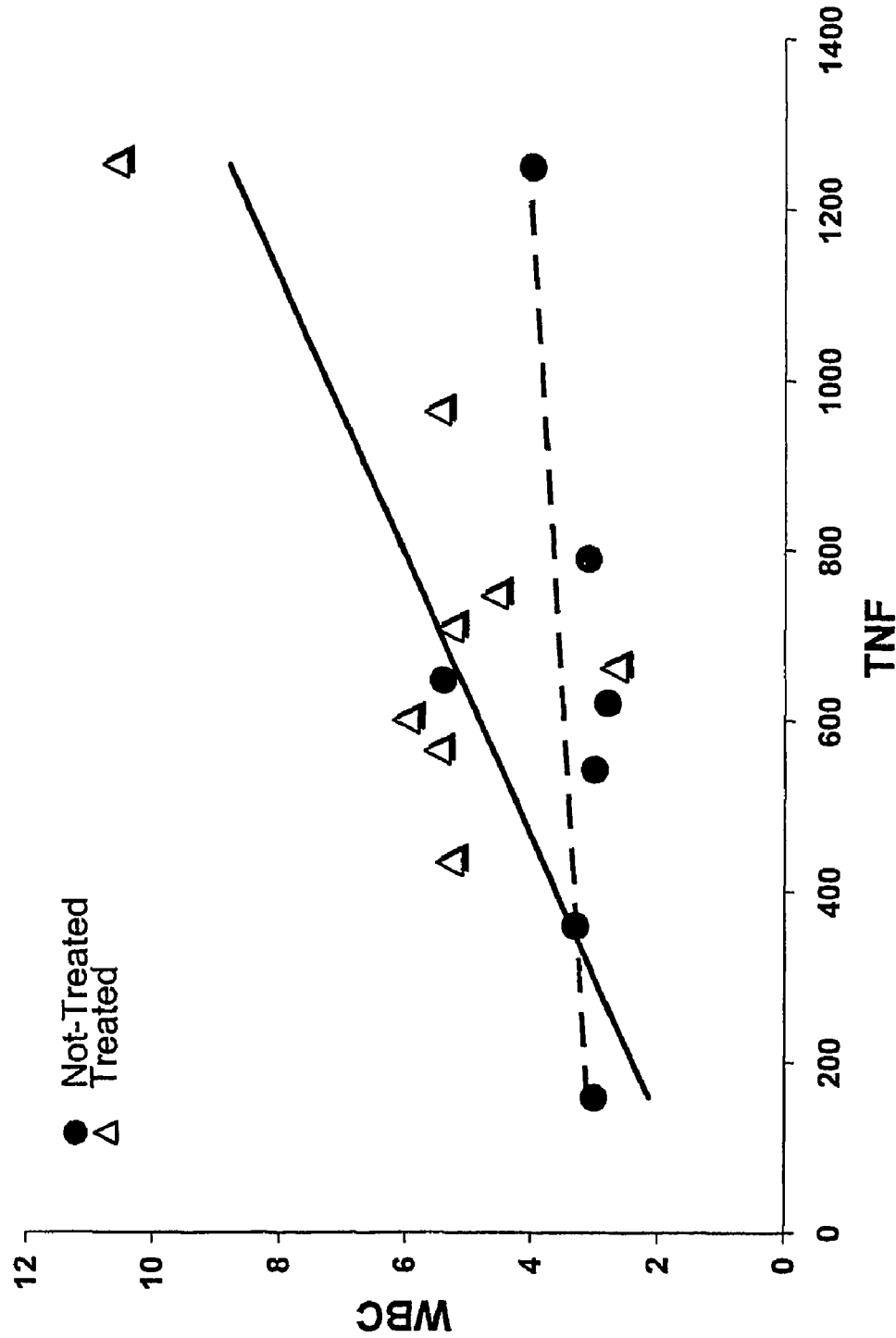
FIG. 4 is a graphic representation of white blood cell count versus TNF-α count for both the treated and control groups, four hours post LPS challenge.

However, Pearson correlation between WBC count and TNF-a concentration of the treated group was highly significant and showed an inverse relation (FIG. 3) at the one-hour mark and a direct correlation 4 hours post challenge (FIG. 4 and Table 8B). The correlations between TNF-α and LDH, GOP and GOT were direct at both points of time. These results are consistent with other results which showed a decrease in WBC concentration at the one-hour mark possibly due to distribution in organ tissues.

While the invention has been described in terms of various preferred embodiments, the skilled person in the art should appreciate that any modifications, substitutions, omissions and other changes may be made without departing from the spirit of the invention and thus any equivalent of the above should be also considered as being part of the scope of the present invention.

The invention claimed is:

1. A method for treating Systemic Inflammatory Response Syndrome (SIRS), comprising:
    administering a composition to a mammal, the composition comprising
    a therapeutically effective amount of venom obtained from at least one venomous snake, and
    a pharmaceutically acceptable carrier, excipient or diluent.

2. The method according to claim 1, wherein the at least one venomous snake is a member of the Viperidae family.

3. The method according to claim 2, wherein the at least one venomous is a *Vipera Aspis* snake.

4. The method according to claim 1, wherein the SIRS is of a non-infectious or infectious origin.

5. A method for treating Systemic Inflammatory Response Syndrome (SIRS) in a mammal, the method comprising:
    administering a pharmaceutical anti-TNF-α composition to the mammal, the composition comprising
    a therapeutically effective amount of venom obtained from at least one venomous snake, and
    a pharmaceutically acceptable carrier, excipient or diluent.

6. A method for treating Systemic Inflammatory Response Syndrome (SIRS) in a mammal, the method comprising:
    administering a pharmaceutical anti-TNF-α composition to the mammal, the composition comprising
    a therapeutically effective amount of venom obtained from at least one venomous snake, and
    a pharmaceutically acceptable carrier, excipient or diluent,
    wherein the composition inhibits TNF-α synthesis, inhibits TNF-α release, or neutralizes TNF-α activity.

* * * * *